United States Patent [19]  [11]  4,102,898
Schneider  [45]  Jul. 25, 1978

[54] ALDEHYDE-CONTAINING THROMBOXANE B, 1,9-LACTONE INTERMEDIATES

[75] Inventor: William P. Schneider, Kalamazoo, Mich.

[73] Assignee: The Upjohn Company, Kalamazoo, Mich.

[21] Appl. No.: 830,539

[22] Filed: Sep. 6, 1977

Related U.S. Application Data

[60] Division of Ser. No. 716,473, Aug. 20, 1976, Pat. No. 4,070,384, which is a continuation-in-part of Ser. No. 676,894, Apr. 14, 1976, Pat. No. 4,018,804.

[51] Int. Cl.$^2$ ............................................. C07D 313/00
[52] U.S. Cl. .................................... 260/343; 542/413; 542/441

[58] Field of Search ................. 260/343; 542/413, 441

[56] References Cited

U.S. PATENT DOCUMENTS 4,049,648  9/1977  Bundy .............................. 260/343.41

Primary Examiner—Natalie Trousof
Assistant Examiner—Jane T. Fan
Attorney, Agent, or Firm—Robert A. Armitage

[57] ABSTRACT

The present specification provides novel intermediates and novel processes for the synthesis of various side chain and skeletal analogs of Thromboxane $B_2$ ($11\beta$-homo-11a-oxa-PGF$_{2\alpha}$). These analogs are particularly and especially useful as reproductive cycle control agents.

2 Claims, No Drawings

ALDEHYDE-CONTAINING THROMBOXANE B, 1,9-LACTONE INTERMEDIATES

CROSS REFERENCE TO RELATED APPLICATION

The present application is a divisional application of Ser. No. 716,473, filed Aug. 20, 1976, now issued as U.S. Pat. No. 4,070,384; which is a continuation-in-part of Ser. No. 676,894, filed Apr. 14. 1976, issued as U.S. Pat. No. 4,018,804 on Apr. 19, 1977.

The present invention relates to processes and intermediates for Thromboxane B compounds for which the essential material constituting a disclosure therefor is incorporated by reference herein from U.S. Pat. No. 4,020,173, issued Apr. 26, 1977 and U.S. Pat. No. 4,070,384, issued Jan. 24, 1978. One species of the present invention is (8S,9R,12S)-8[(1'S)-3'-oxo-1'-hydroxypropyl]-9,12-dihydroxy-cis-5-trans-10-heptadecadienoic acid, 9,12-diacetate, 1,1'-lactone.

I claim:

1. A thromoboxane intermediate of the formula:

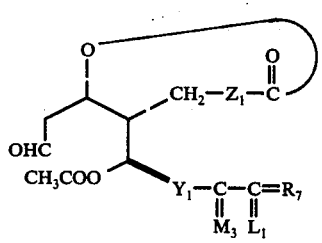

wherein $Z_1$ is
(1) cis—CH=CH—CH$_2$—(CH$_2$)$_g$—CH$_2$—,
(2) cis—CH=CH —CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,

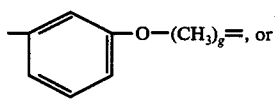 (7)

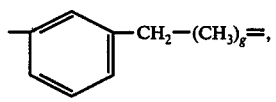 (8)

wherein g is one, 2, or 3;
wherein $Y_1$ is trans—CH=CH— or —CH$_2$—CH$_2$—;
wherein $M_3$ is

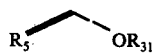

or

-continued

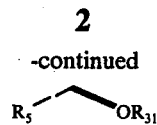

wherein $R_5$ is hydrogen or methyl and $R_{31}$ is a hydroxyhydrogen replacing group;
wherein $L_1$ is

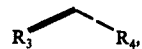

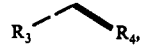

or a mixture of

and

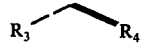

wherein $R_3$ and $R_4$ are hydrogen, methyl, or fluoro, being the same or different with the proviso that one of $R_3$ and $R_4$ is methyl only when the other is hydrogen or methyl; and
wherein $R_7$ is

 (2)

, or

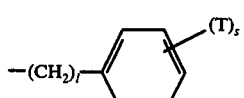 (3)

wherein 1 is zero, one, two, or three,
wherein m is one to 5, inclusive, T is alkyl of one to 3 carbon atoms, inclusive, alkoxy of one to 3 carbon atoms, inclusive, chloro, fluoro, or trifluoromethyl, and s is one, two, or 3, the various T's being the same or different, with the proviso that not more than two T's are other than alkyl, with the further proviso that $R_7$ is

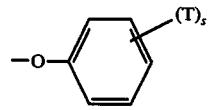

only when $R_3$ and $R_4$ are hydrogen or methyl, being the same or different; and
wherein $R_{33}$ is alkyl of one to 5 carbon atoms, inclusive.

2. (8S,9R,12S)-8[(1'S)-3'-oxo-1'-hydroxypropyl]-9,12-dihydroxy-cis-5-trans-10-heptadecadienoic acid, 9,12-diacetate, 1,1'-lactone, a thromboxane intermediate according to claim 1.

* * * * *

UNITED STATES PATENT OFFICE
CERTIFICATE OF CORRECTION

Patent No. 4,102,898  Dated July 25, 1978

Inventor(s) William P. Schneider

It is certified that error appears in the above-identified patent and that said Letters Patent are hereby corrected as shown below:

Column 1, lines 45-49,

" 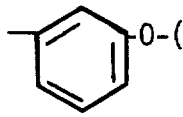, or " should read -- 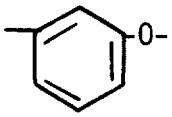, or --;

Column 1, lines 50-54,

" 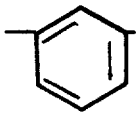, " should read -- , --.

Signed and Sealed this

Twenty-seventh Day of February 1979

[SEAL]

Attest:

RUTH C. MASON
Attesting Officer

DONALD W. BANNER
Commissioner of Patents and Trademarks